United States Patent [19]

Bauer

[11] 4,054,143
[45] Oct. 18, 1977

[54] SINGLE-POLE COAGULATION FORCEPS

[75] Inventor: Siegfried Bauer, Heidelsheim, Germany

[73] Assignee: Richard Wolf GmbH, Knittlingen, Germany

[21] Appl. No.: 678,065

[22] Filed: Apr. 19, 1976

[30] Foreign Application Priority Data

Apr. 26, 1975 Germany .................. 7513534[U]

[51] Int. Cl.² .................. A61B 17/40; A61N 3/06
[52] U.S. Cl. .................................................. 128/303.17
[58] Field of Search ............ 128/303.13, 303.14, 128/303.15, 303.16, 303.17, 407–409

[56] References Cited

U.S. PATENT DOCUMENTS

| 3,805,791 | 4/1974 | Seuberth et al. | 128/303.14 |
| 3,920,021 | 11/1975 | Hiltebrandt | 128/303.17 |
| 3,939,839 | 2/1976 | Curtiss | 128/303.15 |

FOREIGN PATENT DOCUMENTS 702,711  1/1965  Canada .................. 128/303.15

Primary Examiner—Robert W. Michell
Assistant Examiner—Lee S. Cohen
Attorney, Agent, or Firm—Kinzer, Plyer, Dorn & McEachran

[57] ABSTRACT

In a single-pole coagulation forceps having an insulated conductive guide barrel, a rod which is insulated in its proximal end region, which extends through the barrel and which terminates in forceps jaws externally of the distal end of the barrel, and an insulated operated handle connected to the guide barrel and rod, for opening and closing the forceps jaws, there is provided a substantially rigid sheath extending around the insulation of the barrel and an impact and heat-resistant sleeve enclosing said sheath. Preferably, a substantially rigid sheath also extends around the insulation on the proximal end region of the rod and is enclosed by an impact and heat-resistant insulating sleeve.

8 Claims, 4 Drawing Figures

U.S. Patent  Oct. 18, 1977  4,054,143
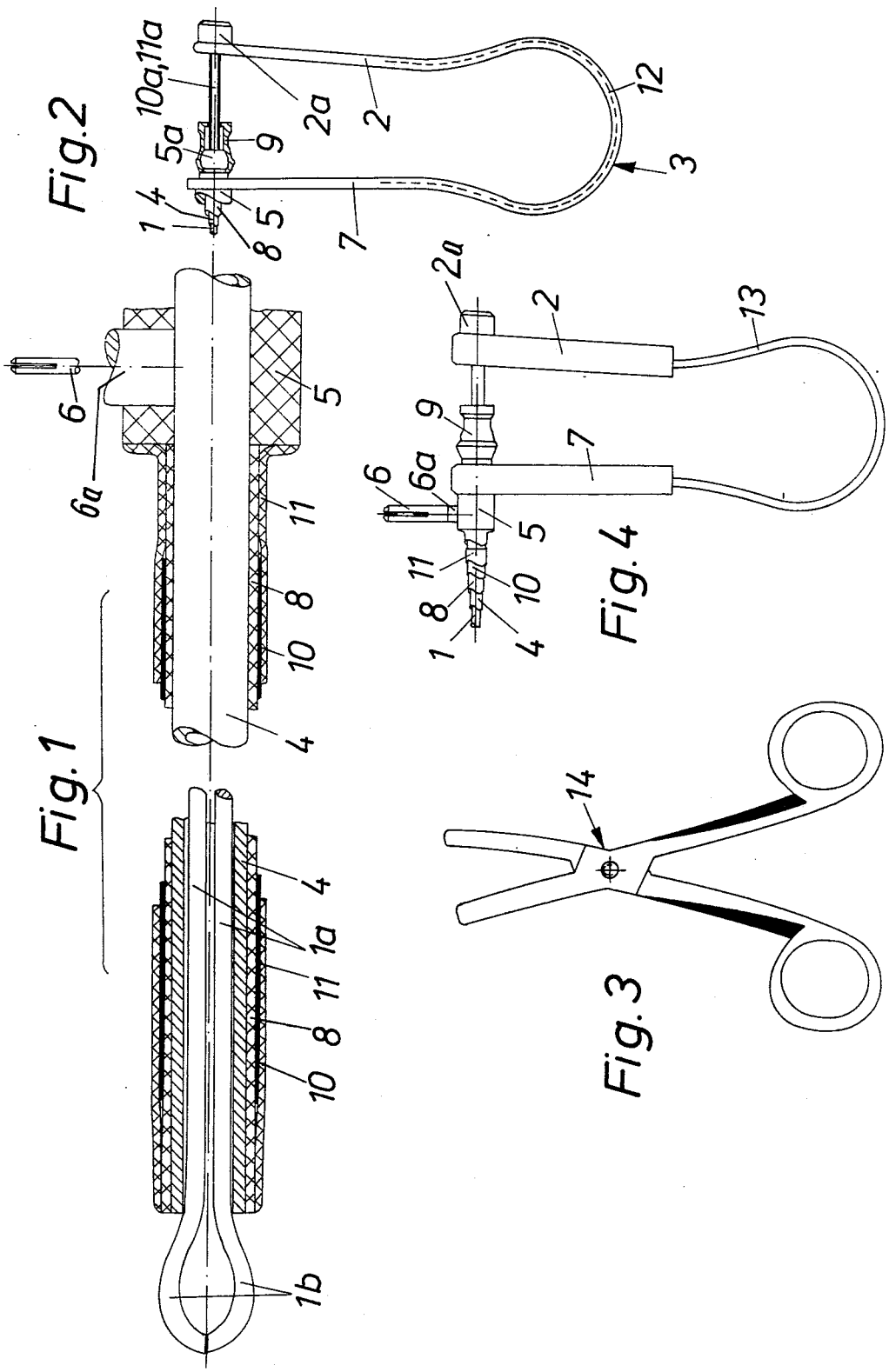

SINGLE-POLE COAGULATION FORCEPS

BACKGROUND OF THE INVENTION

1. Field of the Invention

This invention relates to a single-pole coagulation forceps for endoscopy.

2. Description of the Prior Art

One known coagulation forceps has gripping or forceps arms which are sprung outwards and form the distal end of a traction rod which is insulated for a certain distance at the proximal end. The traction rod extends through a conductive guide barrel which touches the forceps arms, with a seal for the rod at the proximal end, and the barrel is provided with an insulating outer coating and has an HF connection at the proximal end, the barrel and the traction rod being displaceable relative to one another by means of an insulated operating handle to open and close the forceps jaws.

The above measures taken to insulate the guide barrel and the proximal part of the traction rod prevent high-frequency currents, which would be dangerous both for the patient and for the doctor, from being transmitted in an uncontrolled fashion from the barrel to the body of the patient, which acts as an earth, during high frequency coagulation in a body cavity. In practice however it has been shown that total protection is not afforded for the patient even with these insulating precautions, since the plastics insulating coating on the barrel, a possible additional insulating sleeve which there may be surrounding the barrel, and the insulating coating on the proximal part of the traction rod may contain holes or have walls of varying thickness or may become porous or weak after having been used and sterilised a number of times, with the result that the possibility cannot be excluded of currents being transmitted to the patient's body.

An object of the present invention is to provide a single-pole coagulation forceps which affords under normal operating conditions total safety for the patient and the doctor.

SUMMARY OF THE INVENTION

To this end, the invention consists in a single-pole coagulation forceps in which the barrel is additionally surrounded by a rigid or semi-rigid sheath which is enclosed in an impact and heat resistant plastics sleeve.

By means of the invention, the known barrel insulation, consisting of an insulating coating and possibly of an additional insulating sleeve surrounding it, is given additional protection by the rigid metal or insulating sheath, which is in turn protected by the external insulating sleeve, e.g. a shrunk-on sleeve.

Advantageously, the same or similar protection is also provided for the proximal part of the traction rod, which is partly exposed and is provided with an insulating covering.

BRIEF DESCRIPTION OF THE DRAWINGS

FIG. 1 shows an enlarged, interrupted axial section through a coagulation forceps constructed in accordance with the invention, without the proximal section and operating handle, FIG. 2 shows a side view to a reduced scale, partly cut-away, of one form of operating handle, FIG. 3 shows a side view to a reduced scale of another form of operating handle constituted by a scissors grip, FIG. 4 shows yet another operating handle to a reduced scale which is somewhat modified in comparison with the handle of FIG. 2.

BRIEF DESCRIPTION OF THE PREFERRED EMBODIMENTS

The single-pole coagulation forceps contains in a known way a traction rod 1, of which at least the exposed proximal part is surrounded by an insulating covering. The proximal end of the traction rod is mounted in an insulated fashion at 2a in one insulated limb 2 of an operating handle in the form of a spring grip 3 and its distal end is thickened, for a quarter of its length for example, and in the area concerned forms the limbs 1a of the jaws 1b of the forceps, the limbs being sprung (biassed in the direction away from each other) apart and being formed by slotting the rod axially. Conductive traction rod 1 extends through a metal guide barrel 4 and comprises forceps limbs or arms 1a which terminate externally of the distal end of the barrel in forceps jaws 1b. The limbs of the jaws remain in permanent electrically conductive contact with barrel 4. The jaws 1b occupy a normally closed position in which they are maintained by engagement with the distal end of the barrel 4. To open the jaws 1b the spring grip 3 is operated causing the rod to move in the direction of the distal end of the barrel and thus the jaws to disengage from the distal end of the barrel. At the proximal end, the barrel 4 is provided with an insulating strengthener 5. In the area occupied by the strengthener is situated an HF contact 6 which has an insulated bottom part 6a and which is connected to the barrel 4. Also attached at this point is the other limb 7 of the spring grip 3. At the proximal end, reinforced insulating part 5 has an olive 5a onto which is fitted a rubber cap 9 which forms a seal between the barrel 4 and the traction rod 1 to prevent gas, e.g. carbon dioxide or nitrous oxide, escaping from a body cavity.

To prevent HF (high frequency) current used for coagulation being transmitted to the body of the patient through the barrel 4, the barrel is provided with an insulating coating 8 which may additionally be enclosed in an insulating sleeve such as a shrunk-on sleeve.

The barrel insulating coating 8 is enclosed in a protective sheath 10 in the form of a sheath made of metal, glass or ceramics or the like, which is either slid over insulation 8 in the form of a tube or is applied by vapour deposition, spraying or electroplating. This rigid, or in certain circumstances slightly flexible (semi-rigid) sheath 10 is additionally enclosed in an impact and heat-resistant plastics sleeve 11, e.g. a shrunk-on sleeve, in order to provide the sheath 10 with protection in turn, given that under certain circumstances fractures may occur in the glass or ceramic material, and in order in this way to afford protection against current being transmitted to the body of the patient in cases where the sheath 10 is conductive.

Similar measures (10a, 11a) are also advantageously taken in the area where the proximal part of the traction rod 1, which has an insulating coating, is situated. Limbs 2 and 7 of the spring grip 3 are composed of an insulating plastics material in which is embedded a spring 12 which spreads the limbs.

In the modification of FIG. 4 instead of the spring 12 embedded in the insulating plastics material, the ends of a spreader spring 13 are inserted in hollow limbs 2, 7 which are composed of an insulating plastics material and which are connected to the insulating parts 2a and 5 respectively.

Instead of a spring grip operating handle, it is possible to use a scissors grip operating handle 14 as shown in FIG. 3, the jaws and limbs of which are similarly insulated, e.g. they may be provided with a plastics coating or may be composed of glass-fibre-reinforced plastics material, these jaws being connected to the parts 2a and 5.

Various modification may be made without departing from the scope of the invention as defined in the appended claims. For example, any of the illustrated operating handles may be connected to the barrel and traction rod in such manner that the barrel is moved axially with respect to the rod instead of the rod being so moved.

I claim:

1. A single-pole coagulation forceps for endoscopy, comprising:
    a. a conductive guide barrel having proximal and distal ends,
    b. a high frequency connection connected to the barrel in the region of its proximal end,
    c. a conductive rod extending through the guide barrel in electrical conductive contact therewith and comprising forceps arms terminating externally of the distal end of the barrel in forceps jaws and being biased in a direction away from each other,
    d. insulating covering means insulating the end portion of said rod opposite the jaws,
    e. an insulating coating surrounding substantially the length of the barrel,
    f. a substantially rigid sheath extending around substantially the length of said insulating coating,
    g. an impact and heat-resistant insulating sleeve enclosing substantially the length of said sheath and
    h. an insulated operating handle connected to the proximal end of the barrel and the end portion of the rod opposite the jaws for effecting relative displacement of the rod and barrel between positions in which the forceps jaws are closed by engagement with the distal end of the barrel and the forceps jaws are opened by being disengaged from the distal end of the barrel respectively.

2. A single-pole coagulation forceps according to claim 1, wherein a second substantially rigid sheath surrounds said opposite end portion of said rod, which is provided with said insulating covering means, for substantially its entire length and second impact heat-resistant insulating sleeve encloses the second sheath for substantially its entire length.

3. A single-pole coagulation forceps according to claim 1, wherein the substantially rigid sheath is slidably positioned on said insulating coating on the barrel and comprises a one piece tube.

4. A single-pole coagulation forceps according to claim 1, wherein said substantially rigid sheath is in the form of a vapour deposited coating.

5. A single-pole coagulation forceps according to claim 1, wherein said substantially rigid sheath is in the form of a sprayed coating.

6. A single-pole coagulation forceps according to claim 1, wherein said substantially rigid sheath is in the form of an electro-plated coating.

7. A single-pole coagulation forceps as claimed in claim 1, and including a seal at the proximal end of the barrel sealing between the rod and the barrel.

8. A single-pole coagulation forceps as claimed in claim 1, wherein the operating handle comprises spring grips.

* * * * *